US008002707B2

(12) United States Patent
Ooshima

(10) Patent No.: US 8,002,707 B2
(45) Date of Patent: Aug. 23, 2011

(54) APPARATUS WHICH DISPLAYS MEDICAL TREND GRAPH AND RELATED INFORMATION

(75) Inventor: Yasunori Ooshima, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1303 days.

(21) Appl. No.: 10/943,246

(22) Filed: Sep. 17, 2004

(65) Prior Publication Data

US 2005/0096540 A1 May 5, 2005

(30) Foreign Application Priority Data

Sep. 19, 2003 (JP) .................................. 2003-328602

(51) Int. Cl.
*A61B 8/00* (2006.01)
(52) U.S. Cl. ........................................ 600/438; 715/700
(58) Field of Classification Search .................. 600/437, 600/438; 715/700
See application file for complete search history.

(56) References Cited

U.S. PATENT DOCUMENTS

| | | | | |
|---|---|---|---|---|
| 5,749,364 A * | 5/1998 | Sliwa et al. | .................. | 600/438 |
| 5,749,831 A * | 5/1998 | Baker | ........................... | 600/301 |
| 6,907,284 B2 * | 6/2005 | Hamilton et al. | ............. | 600/511 |
| 7,113,819 B2 * | 9/2006 | Hamilton et al. | ............. | 600/511 |
| 7,252,638 B2 * | 8/2007 | Kahn et al. | ..................... | 600/443 |
| 2003/0110503 A1 * | 6/2003 | Perkes | ............................. | 725/86 |
| 2005/0015009 A1 * | 1/2005 | Mourad et al. | ................ | 600/438 |
| 2006/0058650 A1 * | 3/2006 | Sharony | ........................ | 600/437 |
| 2006/0184023 A1 * | 8/2006 | Satoh | ............................. | 600/437 |
| 2006/0247527 A1 * | 11/2006 | Maruyama | .................... | 600/443 |
| 2007/0260142 A1 * | 11/2007 | Kahn et al. | .................... | 600/437 |

FOREIGN PATENT DOCUMENTS

JP 09-327457 12/1997

* cited by examiner

*Primary Examiner* — Brian Casler
*Assistant Examiner* — Amanda Lauritzen
(74) *Attorney, Agent, or Firm* — Oblon, Spivak, McClelland, Maier & Neustadt, L.L.P.

(57) ABSTRACT

An ultrasound diagnosis apparatus including an ultrasound probe, an image processor, a measurement processor, a graph processor, and a display. The ultrasound probe includes a plurality of piezoelectric transducers and is configured to insonify and receive an echo signal resulting from the insonification. The image processor is coupled to the ultrasound probe and is configured to prepare image data based on the echo signal. The measurement processor is coupled to the image processor and is configured to conduct a measurement on the image data with respect to a predetermined parameter. The graph processor is coupled to the measurement processor and is configured to prepare a trend graph based on the measurement when the insonification and the image preparation are conducted more than one time. The display is coupled to the graph processor and is configured to display the trend graph with related information in a time phase on the trend graph.

23 Claims, 12 Drawing Sheets

| BPD | | | | |
|---|---|---|---|---|
| GESTATION PERIOD | MEASUREMENT VALUE | NORMAL AVERAGE | NORMAL UPPER LIMIT | NORMAL LOWER LIMIT |
| 12W | 21mm | 19mm | 23mm | 16mm |
| 13W | 24mm | 22mm | 27mm | 18mm |
| 14W | 26mm | 26mm | 30mm | 21mm |
| 15W | 28mm | 28mm | 33mm | 25mm |
| 16W | 30mm | 32mm | 36mm | 28mm |
| 17W | 31mm | 35mm | 39mm | 31mm |
| 18W | 32mm | 38mm | 43mm | 34mm |

FIG. 4

APPARATUS WHICH DISPLAYS MEDICAL TREND GRAPH AND RELATED INFORMATION

CROSS-REFERENCE TO RELATED APPLICATION

This application is based upon and claims the benefit of priority from Japanese Patent Application No. P2003-328602, filed on Sep. 19, 2003, the entire contents of which are incorporated herein by reference.

BACKGROUND OF THE INVENTION

1. Field of the Invention

The present invention relates to an ultrasound diagnosis apparatus which displays a trend graph based on information acquired by the ultrasound diagnosis apparatus, and also relates to a medical imaging apparatus which displays a trend graph based on information acquired by the medical imaging apparatus. The present invention further relates to an apparatus capable of displaying a trend graph based on information acquired by a medical apparatus. The present invention further relates to a method of displaying a medical trend graph.

2. Description of the Related Art

In a typical ultrasound diagnosis apparatus, transducers built in an ultrasound probe generate ultrasound pulses towards a patient body. The transducers also receive echo signals returning from the patient body as a result of the ultrasound pulse generation. The echo signals occur due to a difference of acoustic impedances among tissues of the patient body. The received echo signals are displayed as ultrasound images on a display monitor. Since the ultrasound diagnosis apparatus requires only simple and easy operations, such as contacting the ultrasound probe with a surface of the patient body for acquiring the ultrasound images (e.g., real-time two-dimensional ultrasound images), the ultrasound diagnosis apparatus is widely used for functional and/or morphological diagnoses of various organs of the patient.

An ultrasound pulse echo technique and an ultrasound Doppler technique have been developed as major techniques in the field of ultrasound diagnoses. These two techniques contribute significantly to progress in obtaining patient body information based on echo signals returned from various organs or blood cells of the patient. Recently, B-mode images acquired by the ultrasound pulse echo technique and color Doppler images (or Doppler-mode images) acquired by the ultrasound Doppler technique are frequently used in ultrasound image diagnoses.

An ultrasound diagnosis technique does not give an exposure affection which may happen in X-ray use and is, therefore, non-invasive to the patient. For this reason, the ultrasound diagnosis technique is particularly often used in an obstetrical service. For example, an ultrasound diagnosis apparatus is typically used to observe an unborn baby, such as an embryo or a fetus in the womb of a pregnant woman, so that various types of diagnoses and treatments can be conducted on the unborn baby.

An ultrasound fetometry is known as one of the ultrasound diagnosis techniques for observing an unborn baby. The fetometry is usually used to measure a shape and a size of one or more organs of the unborn baby in the womb. A blood flow condition of the unborn baby may also be measured in the fetometry. Therefore, the fetometry is known as one of important diagnostic techniques for observing the growth condition of the unborn baby.

In the fetometry at an earlier stage of the pregnancy, a gestational sac (GS) may be measured during the fourth to sixth weeks of the pregnancy. The GS is created in an endometrial cavity as a result of a fertilized egg implanted at a uterine wall. Also, a crown-rump length (CRL) may be measured during the seventh to eleventh weeks of the pregnancy. The CRL is a length from a top of a cephalon to a derriere of the embryo, since the embryo itself can be recognized during the seventh to eleventh weeks of the pregnancy. Further, a biparietal diameter (BPD) may also be measured during the twelfth to twentieth weeks of the pregnancy. The BPD is a diameter of an axial transverse section of the cephalon of the fetus.

In the fetometry at middle and later stages of the pregnancy, the BPD may also be measured. In addition, an occipital frontal diameter (OFD) of a fetal cephalon may be measured. An abdominal circumference (AC) may be measured. Further, for example, a femur length (FL) may be measured, is the FL being a length of a femur along its long axis.

Based on several measurements described above, the growth condition of the unborn baby can be diagnosed. A time-series transition of measurement results (or values) of each measured part (or each parameter) is typically displayed in a form of a trend graph in a display of the ultrasound diagnosis apparatus.

Recently, it has been suggested that such a trend graph can be displayed with ultrasound images used in the measurements on the same screen of a display so that operational and diagnostic efficiency can be improved. One example of such a display technique is described in Japanese Patent Application Publication No. PH09-327457. According to this publication, it is possible to observe a trend graph and ultrasound images at the same time. When, however, a user such as a doctor or a technologist desires to see detailed information and/or related information of the measurement results in each time phase on the trend graph, the user is required to activate another display feature in which such detailed and/or related information is displayed.

For example, the trend graph may include a normal range for measurement results. The normal range may be displayed in addition to the measurement results. When one or more of the measurement results regarding one of the parameters is significantly out of the normal range, the user may want to determine whether the reason is a measurement error or a growth abnormality of the unborn baby. One advantageous way of knowing the reason may be a comparison between the measurement results of the one parameter and measurement results of another parameter, or other parameters, of the same unborn baby. Also, it may be advantageous to refer to trend graph(s) of another one or more of the parameters. As mentioned above, it has been necessary for the user to independently operate or activate a display feature to display additional measurements results and/or trend graphs. In other words, the user has been required to perform many operations for the comparison and reference of patient data, and such operations can be tedious and tiring for the user.

SUMMARY OF THE INVENTION

According to one aspect of the present invention, an ultrasound diagnosis apparatus is provided that includes an ultrasound probe, an image processor, a measurement processor, a graph processor, and a display. The ultrasound probe has a plurality of piezoelectric transducers. The ultrasound probe is configured to insonify and to receive an echo signal resulting from the insonification. The image processor is coupled to the ultrasound probe and is configured to prepare an image data based on the echo signal. The measurement processor is coupled to the image processor and is configured to conduct a measurement on the image data with respect to a predetermined parameter. The graph processor is coupled to the measurement processor and is configured to prepare a trend graph based on the measurement when the insonification and the image preparation are conducted more than one time. The display is coupled to the graph processor and is configured to display the trend graph with related information in a time phase on the trend graph.

According to another aspect of the present invention, a medical imaging apparatus is provided for use in a medical examination. The apparatus includes an acquisition unit, an image processor, a measurement processor, a graph processor, and a display. The acquisition unit is configured to acquire biological information. The image processor is coupled to the acquisition unit and is configured to prepare an image data based on the biological information. The measurement processor is coupled to the image processor and configured to conduct a measurement on the image data with respect to a predetermined parameter. The graph processor is coupled to the measurement processor and is configured to prepare a trend graph based on the measurement when the acquisition and the image preparation are conducted more than one time. The display is coupled to the graph processor and configured to display the trend graph with related information in a time phase on the trend graph.

According to another aspect of the present invention, an apparatus is provided for displaying, the apparatus including an entering unit and a display. The entering unit is configured to enter a trend graph prepared based on medical information acquired more than one time by a medical apparatus and to enter related information in a time phase on the trend graph. The display is coupled to the entering unit and is configured to display the trend graph with the related information.

According to another aspect of the present invention, an apparatus is provided for displaying and includes an entering unit, a graph processor, and a display. The entering unit is configured to enter medical information acquired more than one time by a medical apparatus and to enter related information relating to a time phase of the acquisition. The graph processor is coupled to the entering unit and is configured to prepare a trend graph based on the medical information. The display is coupled to the entering unit and the graph processor and is configured to display the trend graph with the related information.

According to another aspect of the present invention, a method is provided for displaying a trend graph. The method includes acquiring biological information and preparing an image data based on the biological information. The method also includes conducting a measurement on the image data with respect to a predetermined parameter and preparing the trend graph based on the measurement when the acquisition and the image preparation are conducted more than one time. The method further includes displaying the trend graph with related information in a time phase on the trend graph.

According to another aspect of the present invention, an ultrasound diagnosis apparatus is provided that includes an ultrasound probe having a plurality of piezoelectric transducers configured to insonify and receive an echo signal resulting from an insonification. The ultrasound diagnosis apparatus also includes an image processor coupled to the ultrasound probe and configured to prepare image data based on the echo signal, and a measurement processor coupled to the image processor and configured to conduct a measurement on the image data with respect to a predetermined parameter. Also provided is a graph processor coupled to the measurement processor and configured to prepare a trend graph based on the measurement and on previous measurements. In addition, the ultrasound diagnosis apparatus includes means for displaying the trend graph along with related information in a time phase on the trend graph.

According to another aspect of the present invention, a computer program product is provided. The computer program product includes a computer usable medium having computer readable program code embodied in the computer usable medium that, when executed, causes a computer to prepare a plurality of image data based on a plurality of acquired biological information. The computer is also caused, when the code is executed, to conduct a plurality of measurements on the plurality of image data with respect to a predetermined parameter, to prepare a trend graph based on the plurality of measurements, and to control a display unit to display the trend graph with related information in a time phase on the trend graph.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 4 is a chart showing BPD measurement values.

DETAILED DESCRIPTION OF THE PREFERRED EMBODIMENTS

Figure 1:
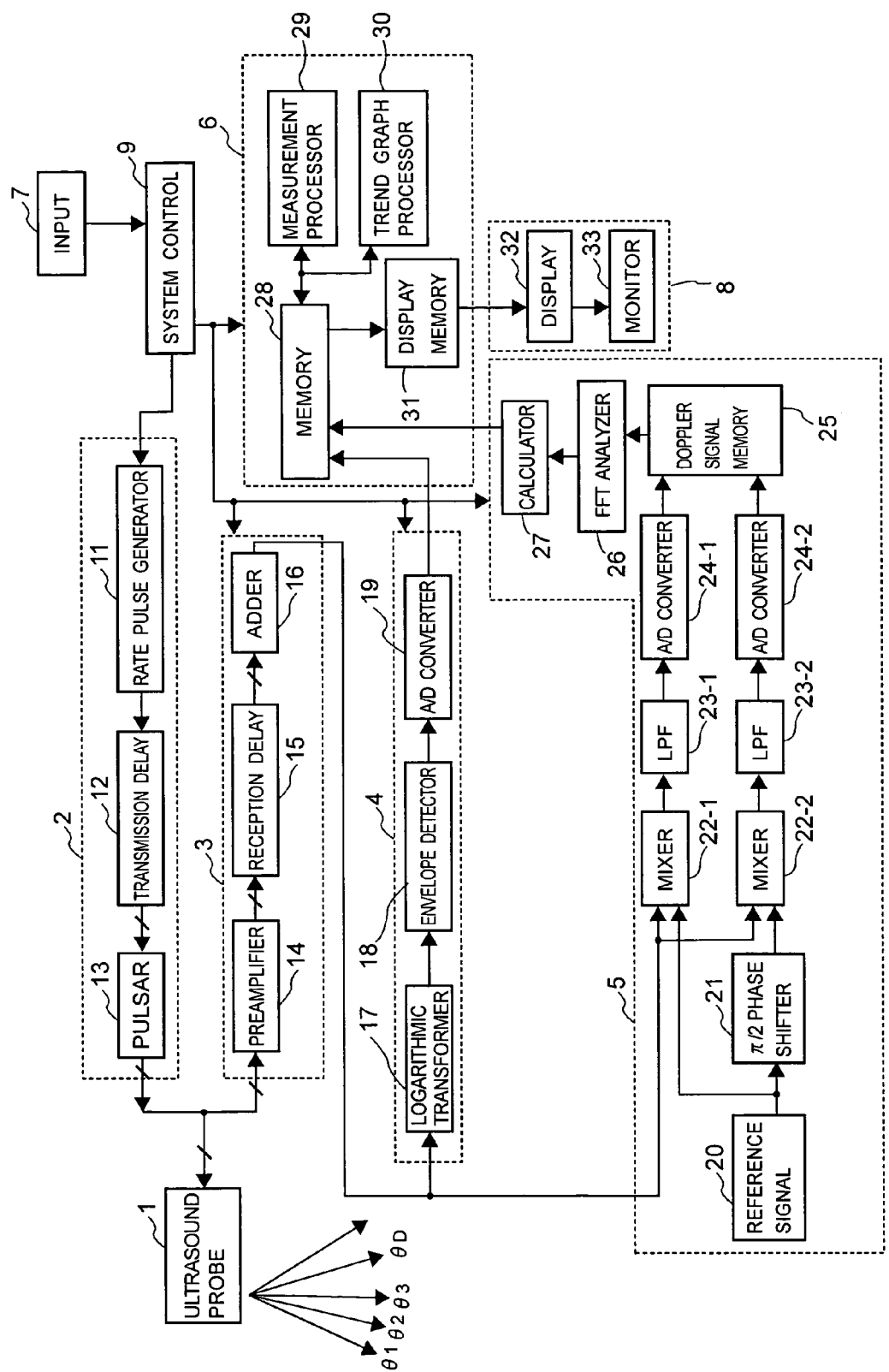
FIG. 1 is a block diagram of an ultrasound diagnosis apparatus in accordance with a first embodiment.

Referring now to the drawings, wherein like reference numerals designate identical or corresponding parts throughout the several views.

An ultrasound diagnosis apparatus will be described below as an example of a medical imaging apparatus. The medical imaging apparatus is not limited to an ultrasound diagnosis apparatus, but can be any medical imaging apparatus acquiring biological information. The medical imaging apparatus can include, for example, an X-ray diagnosis apparatus, an X-ray computed tomography apparatus, a magnetic resonance imaging apparatus, a nuclear medicine diagnosis apparatus, an endoscope, or the like. Data resulting from such an apparatus can be included in the biological information.

FIG. 1 is a block diagram showing an ultrasound diagnosis apparatus according to an embodiment of the present invention. The ultrasound diagnosis apparatus includes an ultrasound probe 1 having a plurality of piezoelectric transducers configured to insonify and receive an echo signal resulting from the insonification. The ultrasound diagnosis apparatus also includes an image processor coupled to the ultrasound probe 1 and configured to prepare an image data based on the echo signal, this image processor corresponding to, for example, a B-mode processing unit 4. Further, the ultrasound diagnosis apparatus includes a Doppler-mode processing unit 5, a memory 28, and a measurement processor 29 coupled to the image processor and configured to conduct a measurement on the image data with respect to a predetermined parameter. A trend graph processor 30 is coupled to the measurement processor 29 and is configured to prepare a trend graph based on the measurement when the insonification and the image preparation are conducted more than one time. The ultrasound diagnosis apparatus further includes a display unit 8 coupled to the trend graph processor 30, the display unit 8 being configured to display the trend graph with related information in a time phase on the trend graph.

The related information can include, but is not limited to, any additional, supplementary, auxiliary, detailed, and/or related information with respect to the measurement in each time phase. For example, the related information can include actual measurement values resulting from the measurement in the measurement processor 29, normal values or ranges in the measurement, a date of examination or insonification, text data input by a user, and/or image data which has been used or referred to in the measurement, in each time phase of one or more parameters of the measurement. The related information can also include transition information of one or more of the parameters. A content of the related information can be defined as a piece of a combination of a plurality of pieces or types of the above-mentioned various kinds of exemplary information.

The details of the ultrasound diagnosis apparatus shown in FIG. 1 is as follows. The ultrasound diagnosis apparatus includes the ultrasound probe 1, an ultrasound transmission unit 2, an ultrasound reception unit 3, the B-mode processing unit 4, the Doppler-mode processing unit 5, an image measurement unit 6, an input unit 7, the display unit 8, and a system control unit 9.

The ultrasound probe 1 can transmit (or insonify) ultrasound pulses and can receive echo signals from a specimen resulting from the transmitted ultrasound pulses while the ultrasound probe 1 is contacting with a body surface of the specimen. The specimen can be a patient, a pregnant woman, an unborn baby (an embryo or a fetus) in the womb of a pregnant woman, or the like. The ultrasound probe 1 includes a top end having a plurality of ultrasound transducers arrayed in one dimension. The ultrasound transducers are formed by piezoelectric transducer elements and convert electric pulses into ultrasound pulses in transmission. Further, the ultrasound transducers convert ultrasound pulses into electric pulses in reception. The ultrasound probe 1 is usually configured to be compact and lightweight, and is coupled to the ultrasound transmission unit 2 and the ultrasound reception unit 3 through a cable. A user such as a doctor or a technologist can select a type of the ultrasound probe 1 according to a part to be diagnosed among, for example, a sector scan, a linear-sector scan, and a convex scan. In the following description, the ultrasound probe 1 will be described with respect to a sector scan.

The ultrasound transmission unit 2 can produce driving signals for generating the ultrasound pulses. The ultrasound transmission unit 2 includes a rate pulse generator 11, a transmission delay circuit 12, and a pulsar 13. The rate pulse generator 11 generates rate pulses, which determine repeated cycles of the ultrasound pulses insonified to the specimen. The generated rate pulses are supplied to the transmission delay circuit 12. The transmission delay circuit 12 is arranged as delay circuitry, which determines a convergent distance and a deflecting angle of an ultrasound beam in transmission. Further, the transmission delay circuit 12 can include a plurality of independent delay circuits. The number of the independent delay circuits to be used can be determined to be the same as that of the ultrasound transducers to be used in transmission. The transmission delay circuit 12 provides the generated rate pulses with a delay time for making the ultrasound pulses converge to a predetermined depth. This is for obtaining a narrow width of the ultrasound beam in transmission. The transmission delay circuit 12 further provides the generated pulses with another delay time for transmitting the ultrasound pulses in a predetermined direction. The delayed rate pulses are supplied to the pulsar 13. The pulsar 13 is arranged as driving circuitry, which produces high voltage pulses for driving the ultrasound transducers. The pulsar 13 can include a plurality of independent driving circuits. The number of the independent driving circuits to be used can be determined to be the same as that of the ultrasound transducers to be used in the transmission, similarly to the transmission delay circuit 12.

The ultrasound reception unit 3 can receive the ultrasound echo signals from the specimen. The ultrasound echo signals result from the ultrasound pulses insonified to the specimen. The ultrasound reception unit 3 includes a preamplifier 14, a reception delay circuit 15, and an adder 16. The preamplifier 14 amplifies signals converted into the electronic pulses by the ultrasound transducers and obtains the electronic pulses, which has a preferable 'signal to noise' (S/N) ratio. The reception delay circuit 15 provides output signals of the preamplifier 14 with a delay time for converging the ultrasound echo signals from a predetermined depth of the specimen (the output signals) so as to obtain a narrow width of an ultrasound beam in reception. The reception delay circuit 15 further provides the output signals with another delay time for sequentially deflecting the ultrasound beam in a predetermined direction and scanning within the specimen. The reception delay circuit 15 supplies the adder 16 with the output signals given both the above delay time and the above another delay time. The adder 16 adds a plurality of the output signals and, accordingly, the plurality of the output signals are output as one ultrasound data signal.

The B-mode processing unit 4 can process the one ultrasound data signal so as to prepare a B-mode image data. The B-mode processing unit 4 includes a logarithmic transformer 17, an envelope detector 18, and an analog-to digital converter (hereinafter referred to as an A/D converter) 19. The logarithmic transformer 17 performs a logarithmic transformation on the amplitude of the one ultrasound data signal so as to emphasize weak elements of the one ultrasound data signal in comparison. Signals received from the insonified specimen can typically have amplitude with a wide dynamic range of more than 80 dB. Therefore, in order to display the signals received from the insonified specimen in a TV monitor with a narrow dynamic range, it is necessary to perform amplitude compression on the signals so as to emphasize the weak elements of the signals. The envelope detector 18 detects envelopes of the one ultrasound data signal on which the logarithmic transformation has already been performed. The envelope detector 18 further removes ultrasonic frequency components of the envelope-detected signal and detects only the amplitude of the signal, which has been removed from the ultrasonic frequency components. The A/D converter 19 converts an output signal of the envelope detector 18 into a digital signal, which represents a B-mode signal.

The Doppler-mode processing unit 5 can process the one ultrasound data signal so as to prepare a Doppler spectrum image data or other types of Doppler-mode image data. The Doppler-mode processing unit 5 includes a reference signal generator 20, a π/2 phase shifter 21, mixers 22-1 and 22-2, low-pass filters 23-1 and 23-2, A/D converters 24-1 and 24-2, a Doppler signal memory 25, a fast Fourier transformation (hereinafter referred to as an FFT) analyzer 26, and a calculator 27. The Doppler-mode processing unit 5 primarily performs a quadrature demodulation and an FFT analysis.

The one ultrasound data signal is input to the first input terminal of the mixer 22-1 and also to the first input terminal of the mixer 22-2. The reference signal generator 20 has a frequency, which is nearly the same as a central frequency of the one ultrasound data signal. The reference signal generator 20 outputs a reference signal, which is directly supplied to the second terminal of the mixer 22-1. The reference signal is also supplied to the π/2 phase shifter 21. The π/2 phase shifter 21 shifts a phase of the reference signal and supplies the second terminal of the mixer 22-2 with a π/2 shifted reference signal. Output signals of the mixers 22-1 and 22-2 are supplied to the low-pass filters 23-1 and 23-2. The low-pass filter 23-1 removes a sum component of a frequency of the reference signal and a frequency of the one ultrasound data signal. Accordingly, a differential component between the frequency of the reference signal and the frequency of the one ultrasound data signal is extracted by the low-pass filter 23-1. Similarly, the low-pass filter 23-2 removes a sum component of a frequency of the π/2 shifted reference signal and the frequency of the one ultrasound data signal. Accordingly, a differential component between the frequency of the π/2 shifted reference signal and the frequency of the one ultrasound data signal is extracted by the low-pass filter 23-2.

The A/D converter 24-1 converts an output of the low-pass filter 23-1 into a digital signal. Similarly, the A/D converter 24-2 converts an output of the low-pass filter 23-2 into a digital signal. In other words, outputs resulting from a quadrature demodulation are converted into digital signals by the A/D converters 24-1 and 24-2. The digitized outputs resulting from the quadrature demodulation are temporarily stored in the Doppler signal memory 25 before supplied to the FFT analyzer 26. The FFT analyzer 26 performs the FFT analysis on the digitized outputs. The calculator 27 calculates a center, an expansion, and the like, of a spectrum obtained from the FFT analyzer 26.

The image measurement unit 6 can conduct measurements on image data acquired in various time phases and can prepare a trend graph based on results of the measurements.

The image measurement unit 6 includes the memory 28, the measurement processor 29, the trend graph processor 30, and a display memory 31. The memory 28 can include a B-mode image memory field, a Doppler-mode image memory field, and a trend data memory field. B-mode data obtained from the B-mode processing unit 4 are stored in the B-mode image memory field in a two-dimensional manner and, accordingly, B-mode image data are prepared. Doppler-mode image data obtained from the Doppler-mode processing unit 5 are stored in the Doppler-mode image memory field in a time-series manner and, accordingly, Doppler-mode image data are prepared. Trend graphs prepared in the trend graph processor 30, and various measured data from the past to the present in the process of the fetal growth, are stored in the trend data memory field when the specimen is an unborn baby. The various measured data can include, for example, the GS, the CRL, the BPD, the OFD, the AC, the FL, and the like. B-mode image data and Doppler-mode image data, which have been used for the measurements, can also be stored as auxiliary information in the trend data memory field.

The measurement processor 29 conducts various measurements on the image data. For example, when a B-mode image is displayed in the display unit 8, the user can designate two points on the displayed image through the input unit 7. The measurement processor 29 can measure the length between the two points. The length can, for example, represent a size of an organ of the unborn baby. In addition, the measurement processor 29 can also conduct measurement on a Doppler-mode image data with respect to the fetal growth measurement. In this case, the measurement can be conducted based on a blood flow in an umbilical artery. The measurements can be of, but not limited to, the GS, the CRL, the BPD, the OFD, the AC, and the FL when the unborn baby is the specimen. The measurement is described in more detail below.

The trend graph processor 30 includes a central processing unit (CPU) and a memory circuit (not shown in FIG. 1). The memory circuit stores normal ranges or normal values of various parameters on each of the predetermined gestation periods or the number of weeks of the pregnancy. The normal values can include an average value of the normal range, an upper limit value of the normal range, and a lower limit value of the normal range, in each time phase of each parameter. The memory circuit can also store software for displaying a trend graph. The CPU reads out the normal values stored in the memory circuit and measurement values stored in the trend data memory field of the memory 28. The CPU then prepares a trend graph of the measurement values in a predetermined format based on the display software stored in the memory circuit.

The display memory 31 temporarily stores image data to be displayed as images in the display unit 8 and other information, such as trend graphs, measurement values, normal values, and the like.

The input unit 7 can include a keyboard, a trackball, a mouse, and/or the like, on an operation panel. The user can operate the input unit 7 so as to determine specimen information, image display modes, acquisition conditions of ultrasound image data, display conditions, measurement parameters, and markers for the measurement. The input unit 7 can also be used to input or select various commands for designating a display of related information in a predetermined time phase on the trend graph.

The display unit 8 includes a display circuit 32 and a monitor 33. The system control unit 9 controls the display memory 31 to read out the B-mode image data, the Doppler-mode image data, the trend graphs, the measurement values, and other necessary information. The display circuit 32 superimposes one or more of the data, the graphs, the values, and the information on other one or more of the data, the graphs, the values, and the information. Here, the superimposition can mean, for example, an overlay or synthesizing two or more of the data, the graphs, the values, and the information. Also, displaying in a form of a pop-up window or a tool tip window can be included in the superimposition. The display circuit 32 converts the superimposed display data to analog signals and also to a TV format. The converted data are displayed in the monitor 33 such as, for example, a CRT (cathode ray tube) or an LCD (liquid crystal display).

The system control unit 9 can include a CPU and a memory (not shown in FIG. 1). Various signals and commands input through the input unit 7 are stored in the memory. The CPU can control several units of the ultrasound diagnosis apparatus and can perform an overall control of the ultrasound diagnosis apparatus, for example, in accordance with the various signals and command input through the input unit 7. The memory of the system control unit 9 can, for example, include a computer readable program code embodied in the memory that, when executed, causes the system control unit 9 to control the measurement processor 29 to conduct a plurality of measurements on a plurality of image data with respect to a predetermined parameter, and to control the trend graph processor 30 to prepare a trend graph based on the plurality of measurements. The computer readable program code can also cause the system control unit 9 to control any of the other processes performed by the ultrasound diagnosis apparatus.

Figure 2:
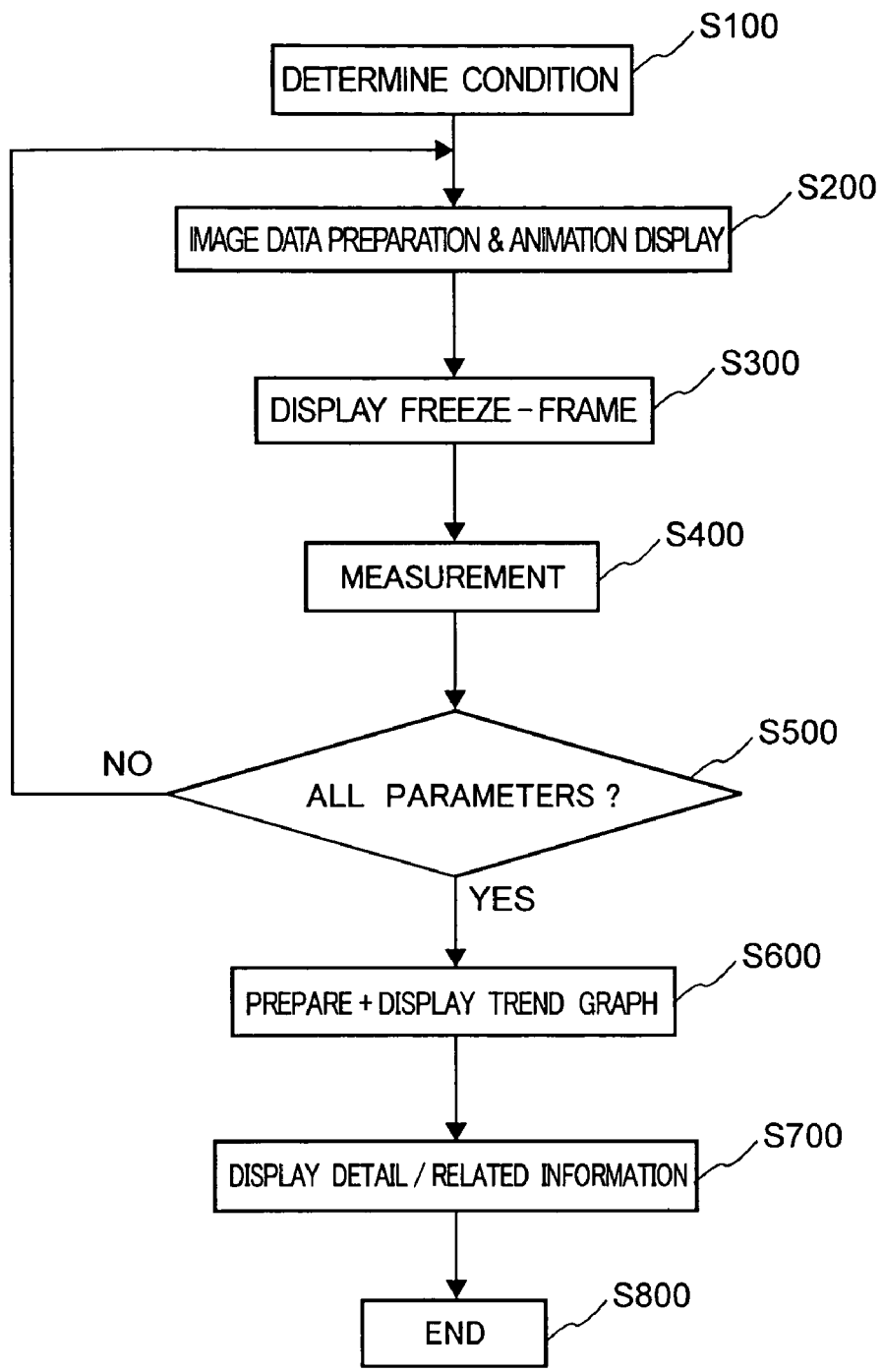
FIG. 2 is a flowchart illustrating data acquisition and the displaying of a trend graph display in the first embodiment.

FIG. 2 is a flowchart showing steps from data acquisition to a trend graph display with related information according to an embodiment of the present invention.

Prior to the ultrasound data acquisition, the user can input one or more of the specimen information, the image display mode, the acquisition condition of ultrasound image data, the display condition, and the parameters through the input unit 7. The input information described above can be set to and stored in the memory of the system control unit 9. For example, the display mode can be determined for displaying B-mode images and Doppler spectrum images (step S100).

Figure 3:
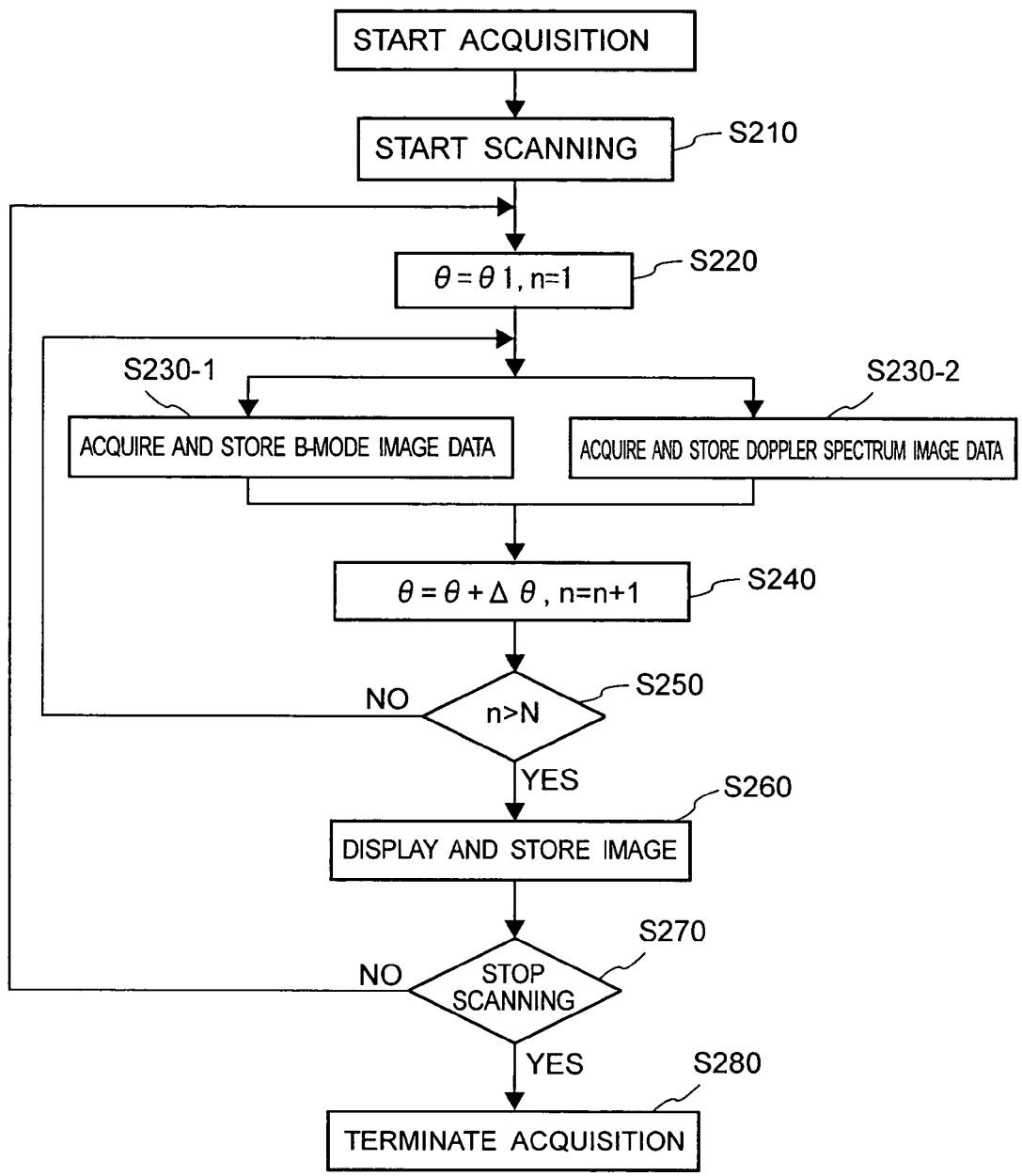
FIG. 3 is a flowchart illustrating an acquisition of image data in the first embodiment.

After the conditions have been determined in step S100, the user can fix the ultrasound probe 1 to a part of an abdomen of a pregnant woman. The part can be appropriate for imaging the unborn baby (embryo or fetus) when the unborn baby is the specimen. Detailed image acquisition will be described with reference to FIG. 3, which is a flowchart showing steps for acquiring image data.

When the user has positioned the ultrasound probe 1 appropriately, a scan is initiated for acquiring the first image data or the first image frame (step S210).

In the ultrasound transmission, the rate pulse generator 11 synchronizes control signals supplied from the system control unit 9. The rate pulse generator 11 generates rate pulses, which determine repeated cycles of the ultrasound pulses insonified to the specimen. The generated rate pulses are supplied to the transmission delay circuit 12. The transmission delay circuit 12 provides the generated rate pulses with a delay time for making the ultrasound pulses converge to a predetermined depth of the unborn baby. This is for obtaining a narrow width of the ultrasound beam in transmission. The transmission delay circuit 12 further provides the generated rate pulses with another delay time for transmitting the ultrasound pulses in the first (n=1) predetermined direction ($\theta$: $\theta=\theta 1$). The transmission will be made in N directions for acquiring the B-mode image data while the Doppler spectrum image data are acquired based on a plurality of transmissions in a specific direction $\theta D$ corresponding to the umbilical artery of the unborn baby. The delayed rate pulses are supplied to the pulsar 13.

The pulsar 13 drives the ultrasound transducers provided in the ultrasound probe 1 with pulses for driving the ultrasound transducers generated responsive to driving rate pulses. Accordingly, the ultrasound pulses are insonified to the inside of the unborn baby through the pregnant woman's body. Part of the ultrasound wave insonified to the unborn baby usually reflects off tissues or borders between organs within the unborn baby, where their acoustic impedances are different. Further, when part of the ultrasound wave reflects off moving reflectors, such as blood cells and heart walls, its ultrasound frequencies are subjected to Doppler-shifts.

The ultrasound waves reflected off the tissues of the specimen can be received as the ultrasound echo signals by the ultrasound transducers. In detail, each of the ultrasound echo signals can be received by each of the ultrasound transducers, which insonified an ultrasound wave resulting in the each ultrasound echo signal. The received ultrasound echo signals are converted into electric signals. The converted electric signals are amplified by the preamplifier 14. The preamplifier 14 can include a plurality of amplifying elements. The number of the amplifying elements to be used can be determined to be the same as that of the ultrasound transducers to be used in the reception. The reception delay circuit 15 receives the preamplified signals. In the reception delay circuit 15, the same number of delay circuits as that of the used ultrasound transducers can be used for the reception.

The reception delay circuit 15 provides the received signals with a delay time for converging the ultrasound echo signals from a predetermined depth (the received signals) so as to obtain a narrow width of an ultrasound beam in reception. The reception delay circuit 15 further provides the received signals with another delay time for receiving the ultrasound beam with strong directional characteristics for the predetermined direction ($\theta=\theta 1$). The reception delay circuit 15 supplies the adder 16 with the received signals given both the above delay time and the above another delay time. The received signals are supplied to the adder 16 from the reception delay circuit 15. The adder 16 adds (or unifies) a plurality of the received signals supplied through the preamplifier 14 and the reception delay circuit 15. Accordingly, the plurality of received signals is output to the B-mode processing unit 4 as one B-mode ultrasound data signal (step S220).

In the B-mode processing unit 4, the logarithmic transformer 17 performs the logarithmic transformation on the one B-mode ultrasound data signal. The envelope detector 18 detects envelopes of the one transformed ultrasound data signal. The one detected ultrasound data signal is converted into a digital signal by the A/D converter 19. The digital signal is sent to and stored in the B-mode image memory field of the memory 28 as the first-direction B-mode image data (step S230-1).

On the other hand, similar ultrasound transmissions and receptions are conducted in the specific direction $\theta D$ so as to acquire the Doppler spectrum image data. Accordingly, a plurality of received signals resulting from the specific direction $\theta D$ is output to the Doppler-mode processing unit 5 as one Doppler spectrum data signal. In the Doppler-mode processing unit 5, the quadrature demodulation is performed on the one Doppler spectrum data signal. The demodulated signal is converted to a complex signal through the mixers 22-1 and 22-2 and the low-pass filter 23-1 and 23-2. The complex signal is converted into a digital signal by the A/D converters 24-1 and 24-2 and is stored in the Doppler signal memory 25 (step S230-2). As will be described below, for the Doppler-mode processing, the scanning by insonifying the ultrasound waves can be performed in the same direction ($\theta D$) several times.

After the storage in steps S230-1 and S230-2, the predetermined direction $\theta$ is changed to the second predetermined direction in a manner following a formula ($\theta=\theta+\Delta\theta$). Since the predetermined direction was $\theta 1$, the second predetermined direction ($\theta$) becomes $\theta 1 + \Delta\theta$ (or $\theta 2$). The 'n' indicating the number of scanning directions is also increased one by one (n=n+1). Therefore, the second predetermined direction (θ1+Δθ) becomes the second (n=2) direction (step S240). However, the direction for the Doppler spectrum data can be kept to be θD. The processing described in steps S230-1, S230-2, and S240 is repeated until the 'n' becomes N (step S250) so that the scanning is performed in N predetermined directions (from the predetermined direction (θ1) to the Nth predetermined direction (θ1+(N−1)Δθ)). The scanning in the N directions is performed for the unborn baby substantially in real time by insonifying the ultrasound waves and receiving the ultrasound echo signals. During the scanning, the system control unit 9 controls the transmission delay circuit 12 and the reception delay circuit 15 to change their delay times in accordance with the N predetermined directions.

Regarding the Doppler spectrum data, a plurality of received signals is obtained with respect to the specific direction θD. For each of the received signals, the processing described in step S230-2 is performed, and accordingly, a plurality of digital complex signals are stored in the Doppler signal memory 25. The FFT analyzer 26 obtains frequency spectrums based on the plurality of digital complex signals stored in the Doppler signal memory 25. The calculator 27 performs a FFT analysis on the Doppler spectrum data signals obtained in twice as a long cycle as the pulse rate and forms a Doppler spectrum in a time-series manner. A result of the calculation is sent to and stored as Doppler spectrum image data in the Doppler-mode image memory field of the memory 28.

The system control unit 9 reads out the B-mode image data stored in the B-mode image memory field of the memory 28 and the Doppler spectrum image data stored in the Doppler-mode image memory field of the memory 28. The system control unit 9 also reads out auxiliary information, such as values and characters accompanying the B-mode image data and the Doppler spectrum image data. The B-mode image data, the Doppler spectrum image data, and the auxiliary information are sent to the display memory 31. In the display memory 31, the B-mode image data, the Doppler spectrum image data, and the auxiliary information are superimposed on each other. The superposed image data is converted into analog signals and TV format in the display circuit 32. The converted image data is displayed on the monitor 33. The B-mode image can alternatively be displayed without the Doppler spectrum image. The superposed image data can also be stored in the memory 28 (step S260).

After the display and the storage in step S260, procedures for the second image data will be prepared so that the second image, that is, the second B-mode image data and the second Doppler spectrum image data, will be acquired at a predetermined frame rate.

The procedures described in steps S220 to S260 will be repeated until the user stops ultrasound scanning operations (step S270). When the user stops the scanning operation, the image data acquisition is terminated (step S280). As a result of repeating the procedures described in steps 220 to 270, the superimposed images are sequentially displayed in the monitor 33 as animation (step S200 in FIG. 2).

The user observes the animated ultrasound images and selects an image which is appropriate for measuring a fetus growth. For example, when the BPD is measured, an image clearly showing a falx cerebri is selected. If necessary, the user changes the position and/or angle of the ultrasound probe 1 so as to obtain such an appropriate image. To select the image, the user operates the input unit 7 so that the animated ultrasound images are frozen at the selected image (or frame) (step S300).

The user can then select a measurement mode and mark both ends of the BPD using the input unit 7. The length of the marked BPD is measured in the measurement processor 29. The measured value is stored in the trend data memory field of the memory 28 (step S400). FIG. 4 illustrates an exemplary table showing BPD measurement values. Whether in a form of a table or not, the measurement BPD value can be stored in relationship to an average of a normal BPD value, an upper limit of a normal BPD value, and a lower limit of a normal BPD value in each week phase or each gestation period. The average, the upper limit, and the lower limit can be calculated statistically or by a regression formula based on clinical data accumulated in the measurements of many normally grown-up unborn babies. Typically, the upper limit and the lower limit can be determined to be values equivalent of $\pm 3\sigma/2$ of a normal distribution of the BPD. The normal BPD values such as the average, the upper limit, and the lower limit can be stored in the trend graph processor 30. In response to the storage of the measurement BPD value, the normal BPD value for the corresponding week to the measurement is read out from the trend graph processor 30 and stored with the measurement BPD value in the trend graph memory field of the memory 28.

The table shown in FIG. 4 is updated according to the repetition of the measurement every week. For example, when the measurement is conducted in the eighteenth week, the measurement BPD value '32 millimeters' is stored and added to the table storing the measurement BPD values of until the seventeenth week.

After the BPD measurement, the measurements can be conducted in the measurement processor 29 with respect to other parameters such as, for example, the CRL, the FL, the OFD, the CC, and the AC, in a similar manner to the BPD measurement. The measurement values are stored in the trend graph memory field of the memory 28. These measurements can be conducted based on the B-mode image data. In addition to the above measurements, the measurement processor 29 can conduct another measurement on the Doppler spectrum image data. The animated Doppler spectrum images can be frozen by the input unit 7, and an appropriate image is selected for the measurement. On the frozen Doppler spectrum image data, the measurement can be conducted, for example, with respect to a blood flow of the umbilical artery. The measurement values are stored in the memory 28.

Figure 5:
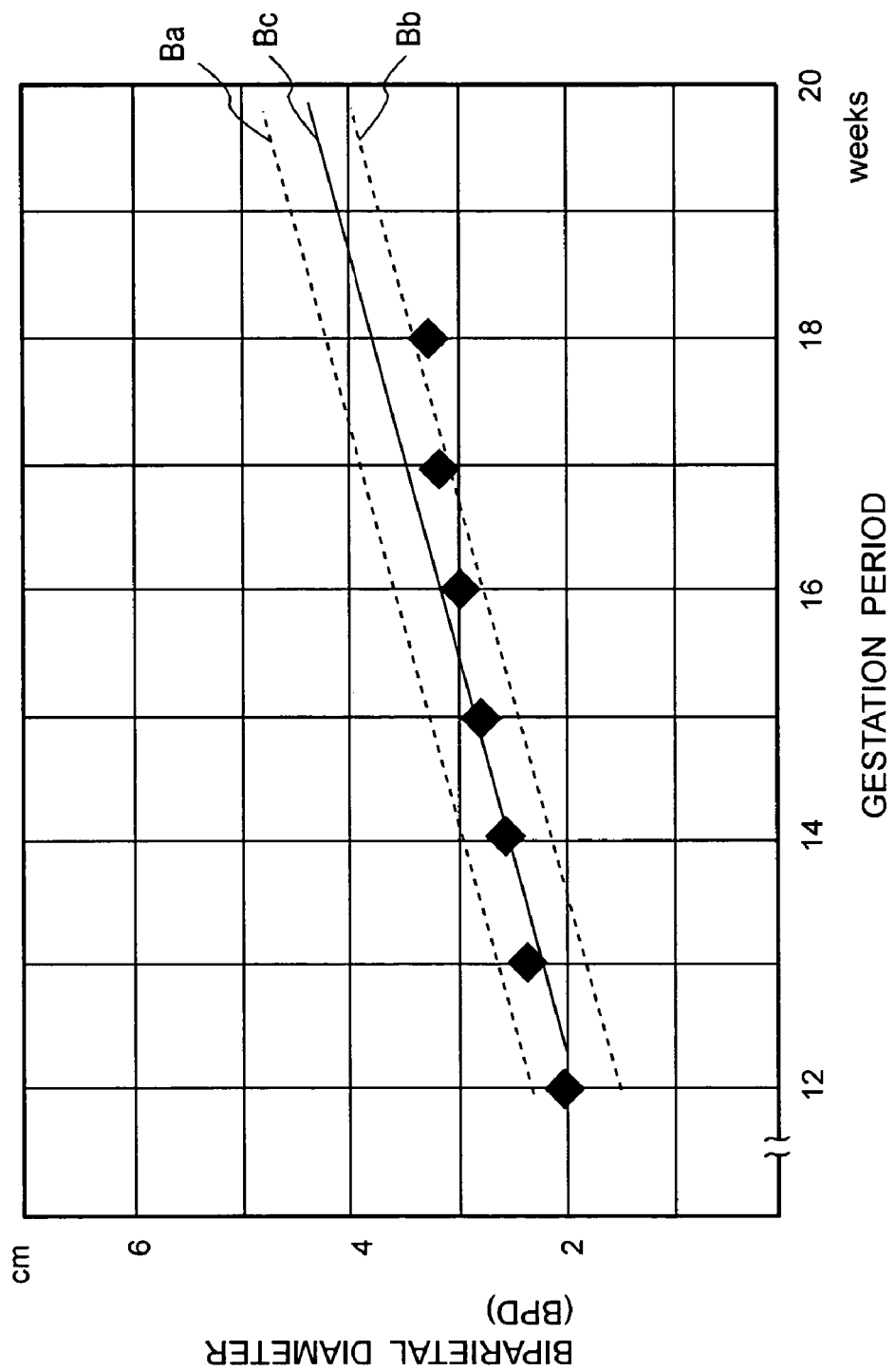
FIG. 5 is a chart showing a trend graph of a BPD.

When the measurement has been conducted on all the parameters (step S500), trend graphs are prepared in the trend graph processor 30 and displayed in the monitor 33 (step S600). For example, in response to a user command for displaying a trend graph of the BPD, command signals based on the input command are sent to the trend graph processor 30 through the system control unit 9. In the trend graph processor 30, the measurement BPD values are read out from the trend graph memory field of the memory 28. The normal BPD values are also read out from the trend graph processor 30. The trend graph processor 30 prepares a BPD trend graph based on the read-out values in accordance with a predetermined format. The prepared BPD trend graph is stored in the trend graph memory field of the memory 28 and is displayed in the monitor 33 through the display memory 31 and the display circuit 32, as shown in FIG. 5. In FIG. 5, the horizontal line represents a gestation period or the number of weeks of the pregnancy. The vertical line represents a length of the BPD. The measurement values which can be obtained every one week are plotted so as to present the BPD trend graph. In the trend graph shown in FIG. 5, Ba indicates an upper limit value of a normal range of the BPD, Bb indicates a lower limit value of the normal range of the BPD, and Bc indicates an average value of the normal range of the BPD.

Figure 6:
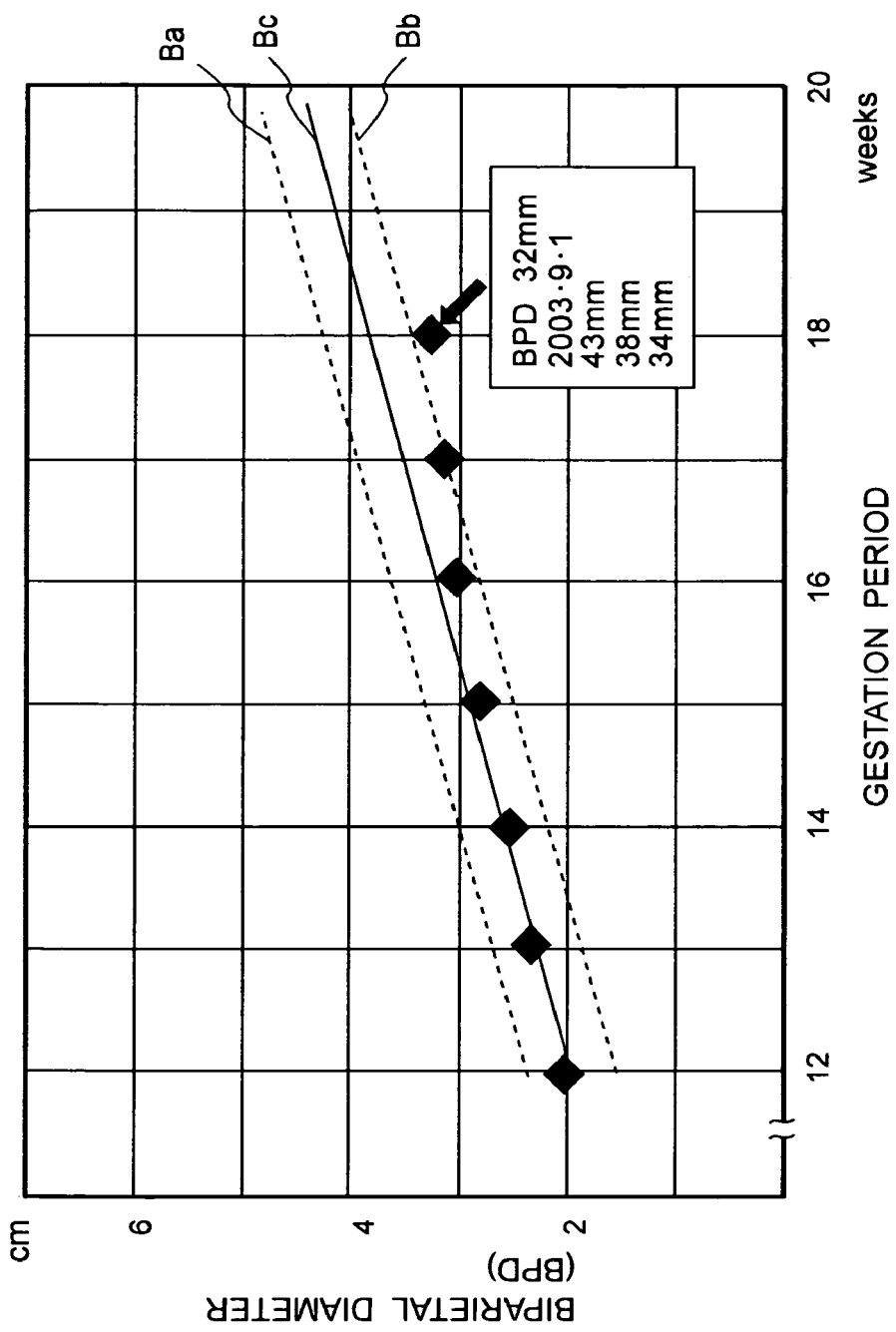
FIG. 6 is a chart showing a first example of a trend graph with related information.

The user can notice that the measurement BPD value in a time phase of the eighteenth week appears to be out of the normal range, that is, lower than the lower limit Bb. The user can then operate the input unit 7 so as to move and position a cursor or a pointer on the mark plotted as the measurement BPD value in the time phase of the eighteen week. In response to the above designation in which the cursor or the pointer is positioned on the plotted mark, related information of the measurement in the time phase of the eighteenth week is displayed near the plotted mark in a form of a tool tip window or a pop-up window as shown in FIG. 6. The related information can include, for example, the measurement BPD value, the date of the measurement or examination (insonification), the upper limit value, the average value, and the lower limit value. The related information in FIG. 6 is superimposed on the trend graph. However, the related information can alternatively be displayed in parallel with the trend graph as shown in FIG. 7.

Figure 7:
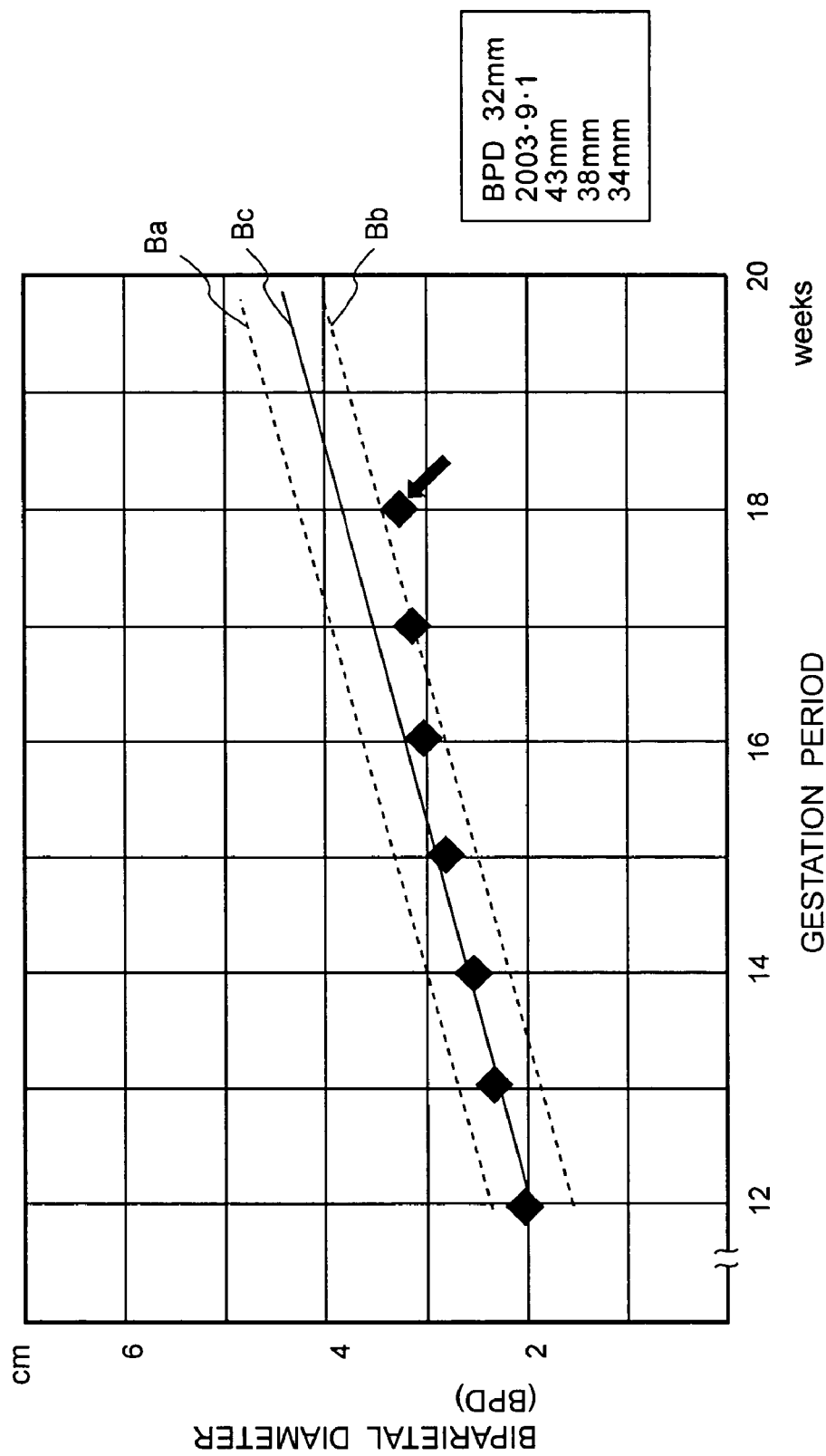
FIG. 7 is a chart showing a second example of a trend graph with related information.
Figure 8:
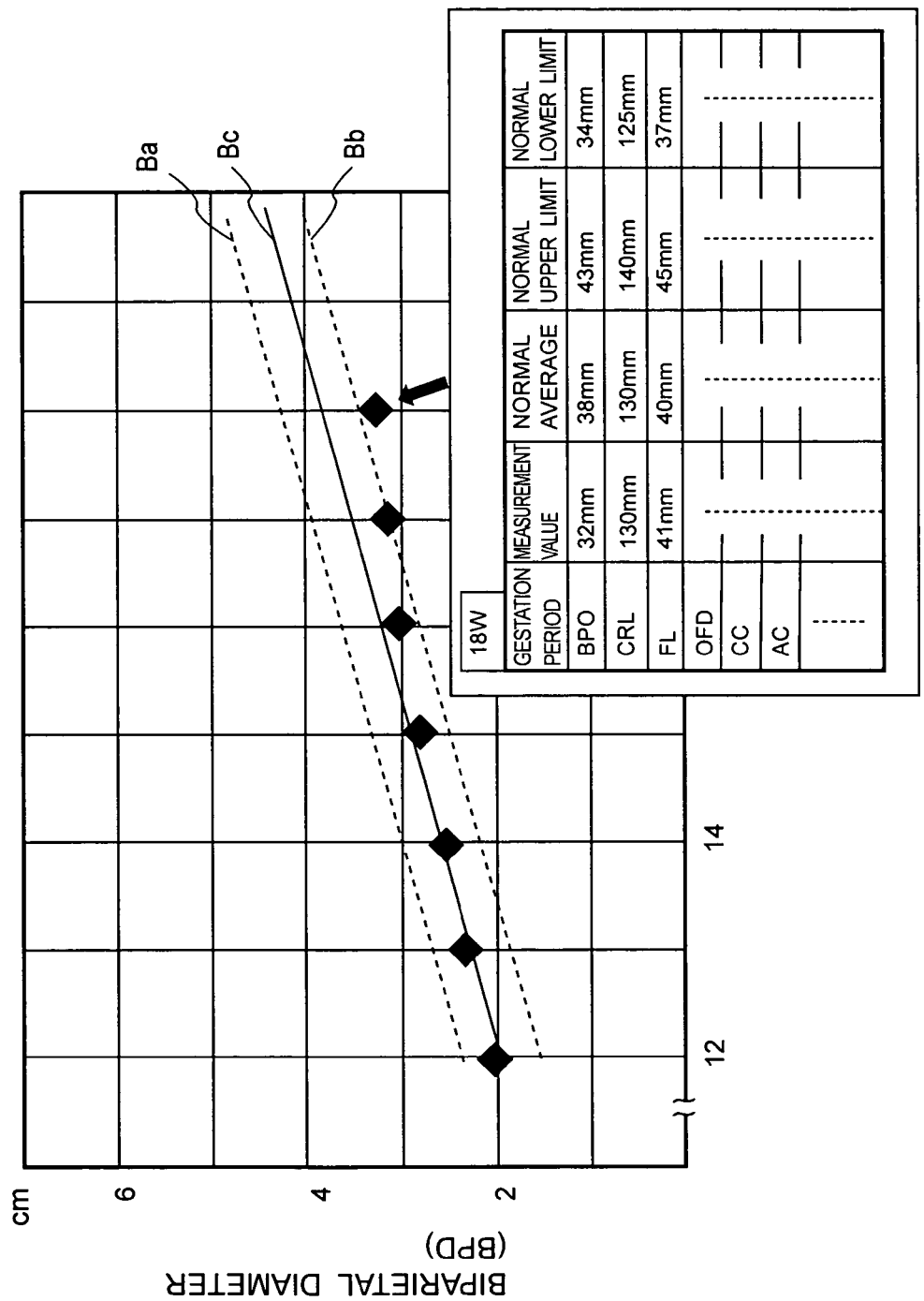
FIG. 8 is a chart showing a third example of a trend graph with related information.

Referring to the related information shown in FIG. 6 or 7, the user can confirm that the measurement BPD value is out of the normal range in the time phase of the eighteenth week. The user can obtain further information, for example, by clicking on the plotted mark. This click-on operation can, for example, be a single click. In response to the click-on operation, related information of the measurement in the time phase of the eighteenth week is displayed near the plotted mark in a form of a tool tip window or a pop-up window as shown in FIG. 8. The related information can be, for example, a table showing the measurement values and normal values of all or part of the parameters in the time phase of the eighteenth week. This table can be prepared in the trend graph processor 30. The trend graph processor 30 reads out the measurement values stored in the trend graph memory field of the memory 28 and the normal values stored in the trend graph processor 30 or the memory 28.

Figure 9:
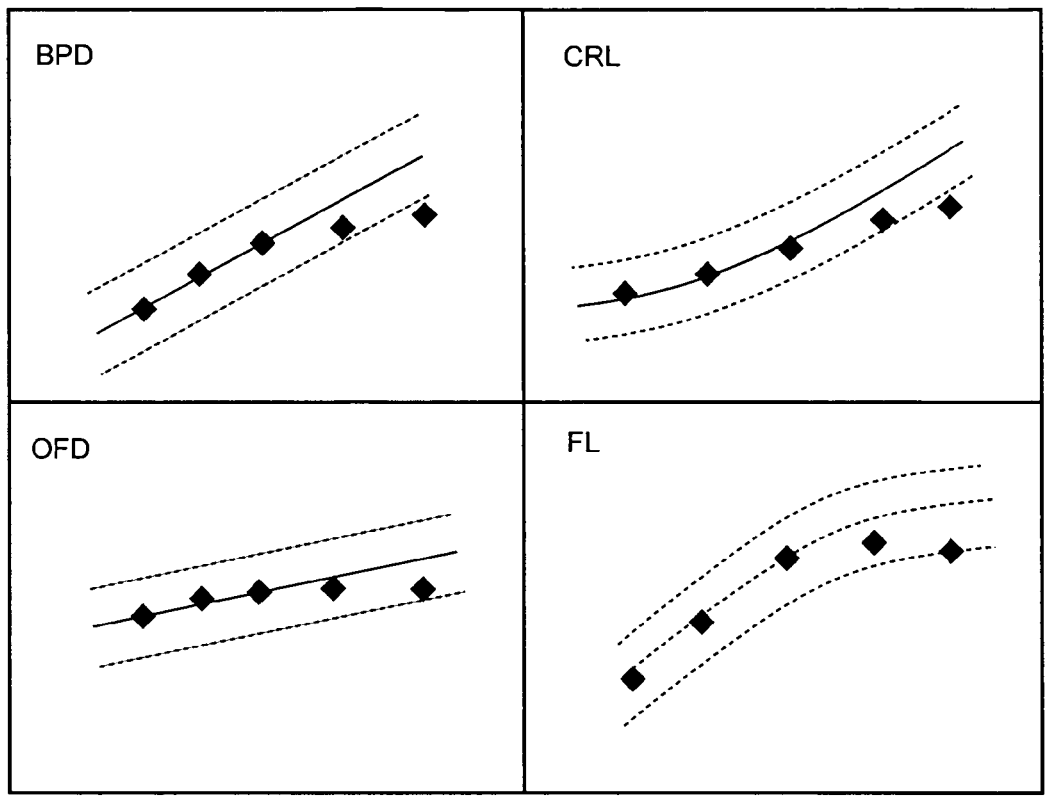
FIG. 9 is an illustration of a parallel display of trend graphs.

Referring to the related information shown in FIG. 8, the user can be able to check whether the reason for the measurement value out of the normal range is because of a measurement error or a growth abnormality of the unborn baby. To further confirm the reason, the user can double-click on the plotted mark. In response to the double-clicking, a plurality of trend graphs can be displayed in the monitor 33. For example, as shown in FIG. 9, trend graphs of the BPD, the CRL, the OFD, and the FL are displayed in parallel as related information. The parameters for the trend graphs as the related information can be determined in advance. Alternatively, the user can select such parameters using the input unit 7 before the double-clicking. The trend graph processor 30 reads out the measurement values of the selected or predetermined parameters stored in the trend graph memory field of the memory 28 and the normal values of such parameters stored in the trend graph processor 30 or the memory 28. The trend graph processor 30 prepares the trend graphs of the parameters based on the read-out values in accordance with a predetermined format.

Referring to the related information shown in FIG. 9, the user can be able to see the transitions of the measurement values of other parameters as well as the BPD. Depending on the transitions, the user can diagnose the unborn baby in suspicion of a growth abnormality (step S700).

When the fetal growth diagnosis has been completed with the trend graph and its related information, the procedure shown in FIG. 2 is ended (step S800). Two or more different contents of the related information can be displayed at the same time in parallel with or superimposed on the trend graph.

According to the embodiment described above, the trend graph is prepared based on the measurement values of the predetermined parameters in a time-series manner. The user can designate a time phase on the trend graph. In response to the designation, related information is superimposed on the trend graph or displayed in parallel with the trend graph. Therefore, it is not necessary for the user to perform independent operations for displaying the related information. This can result in improving examination or diagnosis efficiency. Also, the user can easily compare the measurement values among different parameters and analyze the measurement values from various angles, as shown in FIGS. 6 to 9, for example. Further, diagnosis accuracy can be improved according to the embodiment.

Although the above-described embodiment has been described with respect to measurement on the fetus growth, measurements for other purposes can also be applied. Also, the described embodiment can be modified in various ways. For example, instead of displaying a plurality of trend graphs in parallel as shown in FIG. 9, one or more trend graphs can be superimposed on another trend graph. As with the related information, an image based on the image data used for the measurement can be displayed in parallel with or superimposed on the trend graph.

Figure 10:
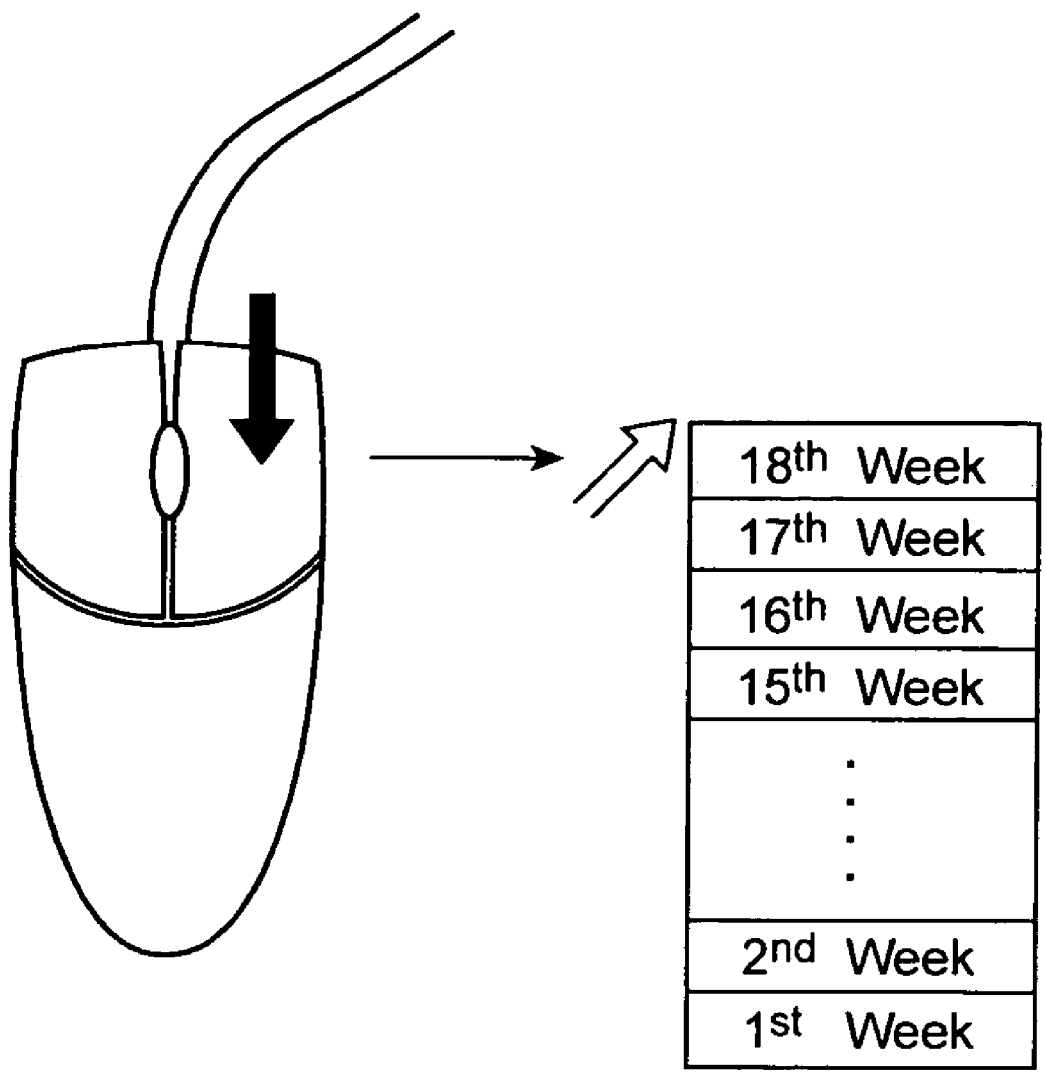
FIG. 10 is an illustration of a mouse that can be used to designate a time phase in the first embodiment.

Instead of positioning a cursor to designate a time phase, a right mouse button of the mouse can, for example, be used, as shown in FIG. 10. In response to press the right mouse button, a list of gestation periods can be displayed. One of the listed gestation periods can be selected to designate the time phase.

Further, alternatively, a touch command screen can be used to designate a time phase or change the already designated time phase of the trend graph. Also the touch command screen can be used to change a displayed content of the related information (e.g. the displayed content in FIG. 6) to other one (e.g. the displayed content in FIG. 8). Still further, a sensor can sense a finger position and motion of the user using, for example, infrared technology. The time phase can be designated or changed in accordance with the sensed position and motion. The sensor can also be used to change a displayed content of the related information (e.g. the displayed content in FIG. 6) to other one (e.g. the displayed content in FIG. 8). Still alternatively, a key input from the keyboard can be used to designate a time phase or to change the already designated time phase of the trend graph. Also, the key input can be used to change a displayed content of the related information (e.g. the displayed content in FIG. 6) to other one (e.g. the displayed content in FIG. 8).

When the related information is displayed in response to the input operation without designating a specific time phase, related information in a predetermined time phase can be displayed on the monitor 33. As an initial display operation, a predetermined initial content of related information in a predetermined time phase can be displayed without any input operation by the input unit 7 at the same time when the trend graph is displayed in the monitor 33. The predetermined time phase can be the latest time phase.

In any case of the embodiment and the above modification, once an initial time phase has been designated or determined, it is not necessary for the user to repeatedly designate a specific time phase for continuous displays in other time phases, but only to press a predetermined button or key to shift the time phase on the trend graph. Similarly, a content of the related information, for example, as shown in FIGS. 6, 8, and 9 can also be shifted in response to a press operation of a predetermined button or key. The predetermined button can include a mouse button.

The user can input text data to be displayed as related information. Although the embodiment has been described that the trend graph is prepared based on the measurement on the B-mode image data and/or the Doppler spectrum image data, a trend graph can be prepared based on other ultrasound image data such as, for example, a color Doppler image data or an ultrasound cardiograph (UCG) data. The related information is obviously not limited to one in the time phase of the eighteenth week, but any time phase according to the necessity.

The above-described display of the trend graph and the related information is not limited to in the described implementation with the ultrasound diagnosis apparatus or medical imaging apparatuses, but can be implemented in another type of display apparatus, such as, for example, a work station, a personal computer, a display terminal, a portable equipment with a display feature, or any other apparatus including a display feature.

Figure 11:
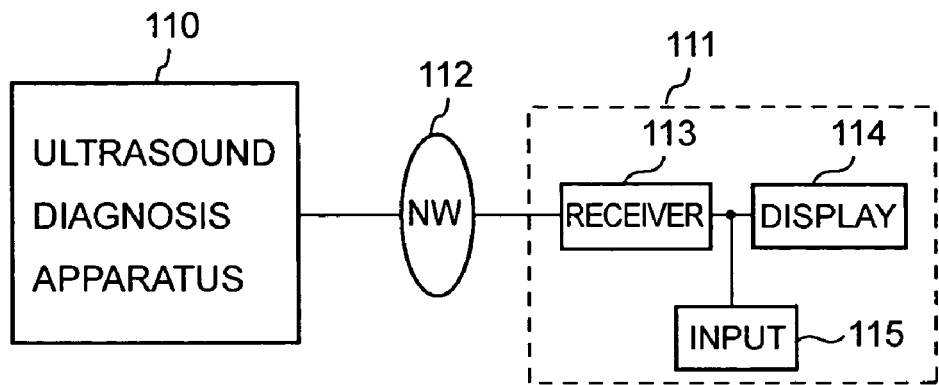
FIG. 11 is a block diagram of a first system including the ultrasound diagnosis apparatus of FIG. 1 and a first display apparatus.

Some examples of such a display apparatus will be explained with reference to FIGS. 11 to 14. As shown in FIG. 11, an ultrasound diagnosis apparatus 110 outputs a trend graph and related information to a display apparatus 111 through a communication network 112. The communication network 112 can be any type of network, such as a wire-based network, a wireless network, or a combination of the two. Here, the communication network 112 can include a communication line to connect the ultrasound diagnosis apparatus 110 and the display apparatus 111. The display apparatus 111 includes a receiver 113, a display 114, and an input unit 115. The receiver 113 operates as an entering unit and receives the trend graph and the related information through the communication network 112. The received trend graph is displayed in the display 114. The display 114 also displays the related information, for example, in response to an input operation by the input unit 115. Therefore, as long as the display apparatus 111 is coupled to the ultrasound diagnosis apparatus 110 via the communication network 112, a user can observe the trend graph with reference to the related information in a remote place, for example, in a consultation room or at a user's home.

Figure 12:
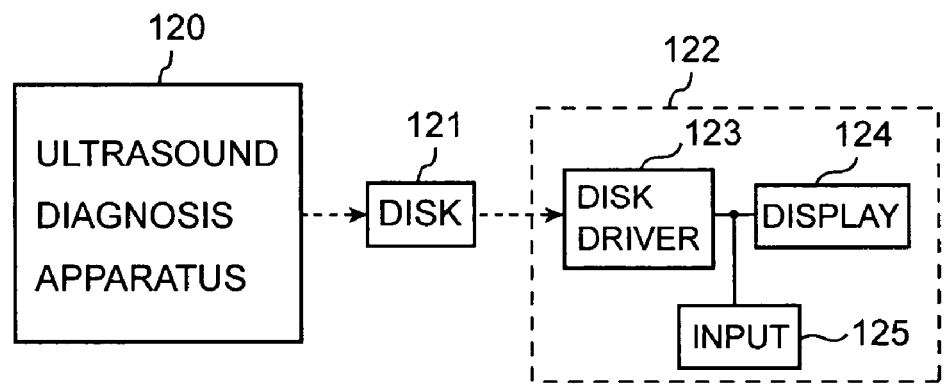
FIG. 12 is a block diagram of a second system including the ultrasound diagnosis apparatus of FIG. 1 and a second display apparatus.

In FIG. 12, an ultrasound diagnosis apparatus 120 writes a trend graph and related information into a portable memory disk (or memory medium) 121. The portable memory disk 121 is detached from the ultrasound diagnosis apparatus 120 and set in a display apparatus 122. The display apparatus 122 includes a disk driver 123, a display 124, and an input unit 125. The portable memory disk 121 is set in the disk driver 123 in which the trend graph and the related information is read out from the portable memory disk 121. The disk driver 123 is operative as an entering unit, and the read-out trend graph is displayed in the display 124. The display 124 also displays the related information in response to an input operation by the input unit 125. Therefore, even if the display apparatus 122 is not directly coupled to the ultrasound diagnosis apparatus 120, a user can observe the trend graph with reference to the related information in a remote place, for example, in a consultation room or at a user's home.

Figure 13:
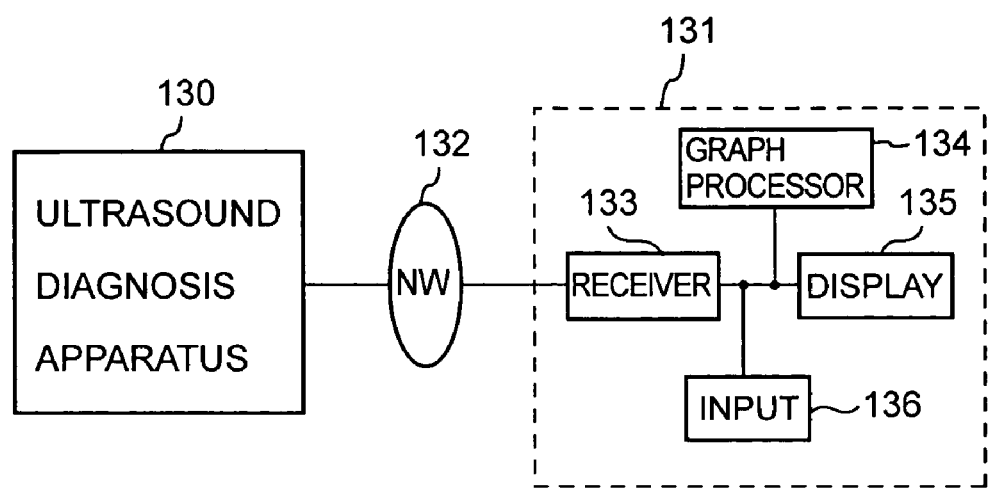
FIG. 13 is a block diagram of a third system including the ultrasound diagnosis apparatus of FIG. 1 and a third display apparatus.

Further, as shown in FIG. 13, an ultrasound diagnosis apparatus 130 outputs medical information including the measurement values to a display apparatus 131 through a communication network 132. The communication network 132 can be any type of network, such as a wire-based network, a wireless network, or a combination of the two. Here, the communication network 132 can include a communication line to connect the ultrasound diagnosis apparatus 130 and the display apparatus 131. The display apparatus 131 includes a receiver 133, a trend graph processor 134, a display 135, and an input unit 136. The receiver 133 is operative as an entering unit and receives the medical information through the communication network 132. The trend graph processor 134 stores the related information, and prepares a trend graph based on the received medical information. The prepared trend graph is displayed in the display 135. The display 135 also displays the related information in response to an input operation by the input unit 136. Therefore, a trend graph can be prepared based on medical information output from the conventional ultrasound diagnosis apparatus without a trend graph preparation feature. A user can observe the trend graph with reference to the related information in a remote place, for example, in a consultation room or at a user's home. If the display apparatus 131 further includes a measurement processor, medical information to be received by the receiver 133 does not need to include the measurement values, but only needs to include image data for measurement.

Figure 14:
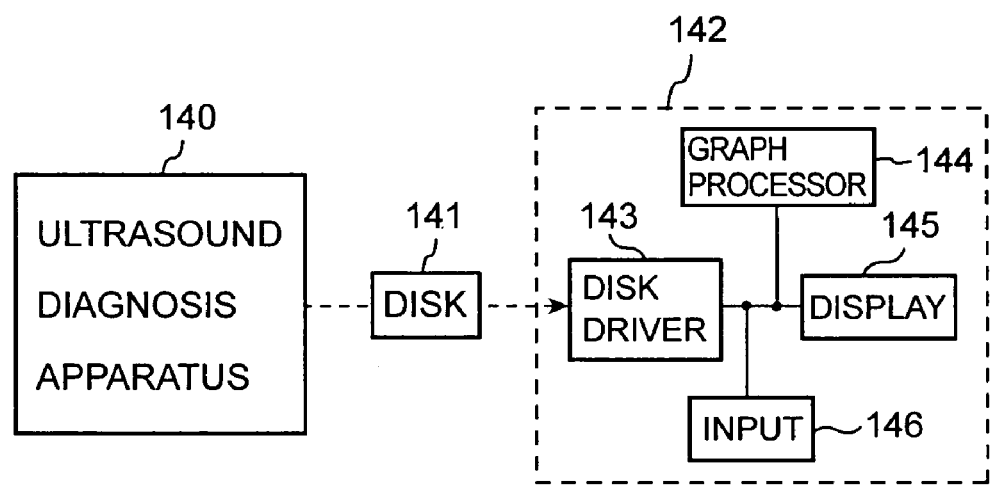
FIG. 14 is a block diagram of a fourth system including the ultrasound diagnosis apparatus of FIG. 1 and a fourth display apparatus.

In FIG. 14, an ultrasound diagnosis apparatus 140 writes medical information including the measurement values into a portable memory disk (or memory medium) 141. The portable memory disk 141 is detached from the ultrasound diagnosis apparatus 140 and set in a display apparatus 142. The display apparatus 142 includes a disk driver 143, a trend graph processor 144, a display 145, and an input unit 146. The portable memory disk 141 is set in the disk driver 143 in which the medical information is read out from the portable memory disk 141. The disk driver 143 is operative as an entering unit, and the trend graph processor 144 stores related information and prepares a trend graph based on the read-out medical information. The prepared trend graph is displayed in the display 145. The display 145 also displays the related information in response to an input operation by the input unit 146. Therefore, a trend graph can be prepared based on medical information output from the conventional ultrasound diagnosis apparatus without a trend graph preparation feature. A user can observe the trend graph with reference to the related information in a remote place, for example, in a consultation room or at a user's home. If the display apparatus 142 further includes a measurement processor, medical information to be read-out from the portable memory disk 141 does not need to include the measurement values, but only needs to include image data for measurement.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnosis apparatus, comprising:
   an ultrasound probe having a plurality of piezoelectric transducers configured to insonify a subject and receive an echo signal resulting from an insonification;
   an image processor coupled to the ultrasound probe and configured to prepare image data based on the echo signal;
   a measurement processor coupled to the image processor and configured to conduct a measurement on the image data with respect to a predetermined feature of the subject;
   a graph processor coupled to the measurement processor and configured to prepare a trend graph based on the measurement when the insonification and an image preparation are conducted for a plurality of time points;
   a display coupled to the graph processor and configured to display the trend graph; and
   an input unit including a user-operative device that is configured to designate a time point of the plurality of time points on the displayed trend graph by positioning a cursor on a time point, wherein a system controller is configured to cause the display to display a first content as related information when the cursor is positioned at the time point without a click-on operation by the user-operative device, wherein the first content includes a date of a measurement corresponding to the designated time point and at least one of a lower limit value, an average value, and an upper limit value, and to cause the display to no longer display the first content, but to display a second content different from the first content as the related information when the cursor is positioned at the time point with a single click-on operation by the user-operative device, wherein the second content includes a plurality of measurement values, other than measurement values displayed on the trend graph, that correspond to the designated time point.

2. The apparatus according to claim 1, wherein the system controller is configured to cause the display to display a third content different from the first content and the second content as the related information when the cursor is positioned at the time point with a double click-on operation by the user-operative device.

3. The apparatus according to claim 1, wherein the system controller is configured to cause the display to display the related information corresponding to the time point, which is predetermined as an initial time point in response to a first input operation of the input unit.

4. The apparatus according to claim 3, wherein the initial time point is a latest time point of the trend graph.

5. The apparatus according to claim 3, wherein the time point is changed in response to a second input operation of the input unit.

6. The apparatus according to claim 1, further comprising:
a key input unit configured to be operable by a user and configured to designate the time point.

7. The apparatus according to claim 1, further comprising:
a key input unit configured to be operable by a user and configured to change the first content of the related information to the second content of the related information.

8. The apparatus according to claim 1, wherein
the system controller is configured to cause the display to display the related information corresponding to the time point that is predetermined as an initial time point without the input unit, and
the time point is changed in response to the input unit.

9. The apparatus according to claim 1, further comprising:
a touch command screen coupled to the display and configured to input second information from a user, wherein the time point is changed in response to the second information.

10. The apparatus according to claim 1, further comprising a touch command screen coupled to the display and configured to input second information in accordance with a user's touch to the touch command screen, wherein the related information is changed from the first content to the second content in response to the second information.

11. The apparatus according to claim 1, further comprising:
a sensor configured to sense at least one of a position and a movement of a user, wherein the time point is changed in accordance with the sensor.

12. The apparatus according to claim 1, further comprising a sensor configured to sense a user, wherein the related information is changed from the first content to the second content in accordance with the sensor.

13. The apparatus according to claim 1, further comprising:
a mouse unit configured to designate the time point based on information specifying the time point selected through a right mouse button of the mouse unit, wherein the system controller is configured to cause the display to display the related information corresponding to the time point designated by the mouse unit.

14. The apparatus according to claim 1, wherein the system controller is configured to cause the display to display the related information superimposed on the trend graph.

15. The apparatus according to claim 1, wherein the system controller is configured to cause the display to display the related information in parallel with the trend graph on the display.

16. The apparatus according to claim 1, wherein the predetermined feature is a growth of an unborn baby when the ultrasound probe insonifies towards the unborn baby.

17. The apparatus according to claim 1, further comprising:
a memory coupled to the graph processor and configured to store a normal value of the predetermined parameter, wherein the graph processor is configured to prepare the trend graph based on the normal value and on a measurement value measured by the measurement processor with respect to the predetermined parameter.

18. The apparatus according to claim 1, wherein,
the graph processor is further configured to prepare a second trend graph based on a measurement by the measurement processor with respect to a feature other than the predetermined feature, and
the system controller is configured to cause the display to display the second trend graph with the trend graph.

19. The apparatus according to claim 1, wherein the system controller is configured to cause the display to display at least one of a measurement value measured by the measurement processor with respect to the predetermined feature at the time point, a normal value of the predetermined feature at the time point, and a date of the insonification as the related information.

20. The apparatus according to claim 1, wherein the system controller is configured to cause the display to display a measurement value measured by the measurement processor with respect to a feature other than the predetermined feature at a time point identical to the time point as the related information.

21. The apparatus according to claim 1, wherein the system controller is configured to cause the display to display the related information in a field of one of a pop-up window and a tool tip window.

22. The apparatus according to claim 1, wherein the system controller is configured to cause the display to display an image based on the image data corresponding to the time point as the related information.

23. The apparatus according to claim 1,
wherein the input unit is configured to input text data for the time point, wherein the system controller is configured to cause the display to display the text data as the related information.

* * * * *